(12) United States Patent
Morifuji et al.

(10) Patent No.: US 11,684,644 B2
(45) Date of Patent: Jun. 27, 2023

(54) COMPOSITION FOR PROMOTING ABSORPTION OF PHYTOCHEMICALS

(71) Applicant: MEIJI CO., LTD., Tokyo (JP)

(72) Inventors: Masashi Morifuji, Tokyo (JP); Masami Kitade, Tokyo (JP); Satomi Ichikawa, Tokyo (JP)

(73) Assignee: MEIJI CO., LTD., Tokyo (JP)

( * ) Notice: Subject to any disclaimer, the term of this patent is extended or adjusted under 35 U.S.C. 154(b) by 0 days.

(21) Appl. No.: 17/266,291

(22) PCT Filed: Aug. 7, 2019

(86) PCT No.: PCT/JP2019/031112
§ 371 (c)(1),
(2) Date: Feb. 5, 2021

(87) PCT Pub. No.: WO2020/032100
PCT Pub. Date: Feb. 13, 2020

(65) Prior Publication Data
US 2021/0299194 A1 Sep. 30, 2021

(30) Foreign Application Priority Data
Aug. 8, 2018 (JP) ................................. 2018-149303

(51) Int. Cl.
| | |
|---|---|
| *A61K 35/747* | (2015.01) |
| *A23C 9/123* | (2006.01) |
| *A61K 35/20* | (2006.01) |
| *A61K 35/744* | (2015.01) |
| *A61P 3/02* | (2006.01) |
| *A61K 9/00* | (2006.01) |

(52) U.S. Cl.
CPC .......... *A61K 35/747* (2013.01); *A23C 9/1238* (2013.01); *A61K 9/0056* (2013.01); *A61K 35/20* (2013.01); *A61K 35/744* (2013.01); *A61P 3/02* (2018.01); *A23Y 2220/15* (2013.01); *A23Y 2240/75* (2013.01)

(58) Field of Classification Search
None
See application file for complete search history.

(56) References Cited

U.S. PATENT DOCUMENTS

| | | | | |
|---|---|---|---|---|
| 4,965,079 A | * | 10/1990 | Hose ..................... | A23C 9/1238 426/583 |
| 11,160,288 B2 | * | 11/2021 | Christensen ......... | C07K 14/315 |

FOREIGN PATENT DOCUMENTS

| | | |
|---|---|---|
| JP | 2010-24230 | 2/2010 |
| WO | WO 2014/091988 | * 6/2014 |
| WO | WO 2015/068790 | * 5/2015 |

OTHER PUBLICATIONS

Bartkiene et al. Food Technol. Biotechnol. 2013, 51(4), pp. 471-478.*
International Preliminary Report on Patentability dated Feb. 9, 2021 in International (PCT) Application No. PCT/JP2019/031112.
Office Action dated Dec. 20, 2022 in corresponding Chinese Patent Application No. 201980066521.8, with English-language translation.
Lee, Na-Kyoung et al., "Bioconversion Using Lactic Acid Bacteria: Ginsenosides, GABA, and Phenolic Compounds", Journal of Microbiology and Biotechnology, May 2017, vol. 27, No. 5, pp. 869-877.
Ding, W.K. et al., "Enhancing the Biotransformation of Isoflavones in Soymilk Supplemented with Lactose Using Probiotic Bacteria during Extended Fermentation", Journal of Food Science, 2010, vol. 75, No. 3.
Office Action dated May 11, 2023, in corresponding Chinese Application No. 201980066521.8, with English translation.

* cited by examiner

*Primary Examiner* — Vera Afremova
(74) *Attorney, Agent, or Firm* — Wenderoth, Lind & Ponack, L.L.P.

(57) ABSTRACT

Disclosed is a composition for promoting absorption of a poorly water-soluble phytochemical which can significantly improve the intake of a phytochemical into a body, especially a migration speed and/or a migration amount of the phytochemical into a blood. A polysaccharide-containing lactic acid bacterial product, which is produced by *Lactobacillus delbrueckii* ssp. *bulgaricus* OLL1251, can significantly enhance the intake of a phytochemical into a body, especially a migration speed and/or a migration amount of the phytochemical into a blood. Thus, the composition for promoting absorption of a phytochemical according to the present invention includes, as an active ingredient, the polysaccharide-containing lactic acid bacterial product. Furthermore, the composition for promoting absorption of a phytochemical is useful as a food additive composition. In addition, a food, or a beverage, or a food or beverage composition to which the composition for promoting absorption of a phytochemical is added can obtain an effect of promoting absorption of phytochemical.

17 Claims, 2 Drawing Sheets

COMPOSITION FOR PROMOTING ABSORPTION OF PHYTOCHEMICALS

TECHNICAL FIELD

The present invention relates to a composition for promoting absorption of a phytochemical, having an action of promoting absorption of a poorly water-soluble phytochemical into a body.

BACKGROUND ART

Phytochemicals generally mean compounds that are originated from a plant and not essential to keep a usual body function but have a favorable effect on a health condition. For example, isoflavone, which is a polyphenol, is much included in soybeans and has functions of healing a menopause disorder and preventing an osteoporosis; quercetin is much included in an onion and has functions of improving a blood flow and reducing a body fat; β-carotene, which is a terpenoid, is much included in a carrot and a pumpkin, and has functions of maintaining a visual function, an internal mucosa membrane and a skin, and an immune function; and lycopene is much included in a tomato and has functions of decreasing a blood cholesterol and a blood pressure.

It is known in the art that many phytochemicals are decomposed by being processed and cooked, and eventually disappears, and also known that their migration into a body is sluggish due to many poorly water-soluble components contained therein, illustrative examples of the popular method for promoting absorption of the poorly water-soluble phytochemical include a method of improving solubility and dispersibility of the phytochemical by its emulsification and formulation, a method of making a particle diameter of the phytochemical smaller, and a method of amorphizing the phytochemical.

Furthermore, as a method for promoting absorption of the poorly water-soluble phytochemical, for example, JP 2016-216440 A (PTL 1) discloses, as catechins-absorbing promotor, at least one selected from the group consisting of resveratrol, hesperetin, extract from a luo han guo (*Siraitia grosvenorii*), extract from a red date (*Zizyphus jujuba* var. *inermis*), extract from a lime (*Citrus aurantiifolia*), extract from a lemon (*Citrus limon*), extract from a pineapple (*Ananas comosus*), apigenin, glucose, difructose dianhydride III, sucralose, aspartame or a salt thereof, erythritol, inositol, citric acid or a salt thereof, phytic acid or a salt thereof, and gallic acid or a salt thereof.

JP 2016-93143 A (PTL 2) discloses that when a polyphenol such as catechin having low bioavailability is added to a prescribed blend of a fat and a hydrocarbon, absorption of the polyphenol such as catechin as well as accumulation thereof in a blood plasma can be enhanced.

JP 2016-506381 A (PTL 3) discloses an enhancer of the bioavailability of catechin, containing cyclodextrin as an active ingredient.

However, these PTLs do not disclose that a lactic acid bacterial product, which contains a polysaccharide as an active ingredient, has an action of promoting absorption of a phytochemical.

On the other hand, a combination of a lactic acid bacterium and a phytochemical is disclosed, for example, in JP H08-322464 A (PTL 4). This literature discloses fermented milk obtained by adding about 0.1 to about 2,000 ppm of catechin and tocopherol, respectively, to yogurt containing a lactic acid bacterium and a *Bifidobacterium*, thereby increasing a productivity of the *Bifidobacterium*. Furthermore, JP 2015-527076 A (PTL 5) discloses a method for producing a nutrient composition based on a richly-textured milk product, containing a phytochemical. However, none of these PTLs discloses that a lactic acid bacterial product has an action of promoting absorption of a phytochemical.

A part of the inventors of the present invention previously found that a polysaccharide-containing lactic acid bacterial product significantly improved the intake of a poorly water-soluble phytochemical into a body, especially a migration speed and/or a migration amount of the phytochemical into a blood; and thus, suggested providing a composition having an action of promoting absorption of the poorly water-soluble phytochemical into a body (PCT/JP2018/010366).

CITATION LIST

Patent Literature

[PTL 1] JP 2016-216440 A
[PTL 2] JP 2016-93143 A
[PTL 3] JP 2016-506381 A
[PTL 4] JP H08-322464 A
[PTL 5] JP 2015-527076 A

SUMMARY OF THE INVENTION

Technical Problem

The inventors of the present invention have now found that a polysaccharide-containing lactic acid bacterial product produced by a particular strain is capable of significantly promoting the intake of a poorly water-soluble phytochemical into a body, especially a migration speed and/or a migration amount of the phytochemical into a blood.

Furthermore, in the previously suggested composition for promoting absorption of phytochemical, it has been found that the polysaccharide-containing lactic acid bacterial product is able to be efficiently produced by the combination of particular strains. The present invention was accomplished on the basis of these findings.

Accordingly, the present invention has an object to provide a composition for promoting absorption of a phytochemical, which has an action of promoting absorption of a poorly water-soluble phytochemical into a body.

In addition, the present invention has an object to provide a food additive comprising the composition for promoting absorption of a poorly water-soluble phytochemical, as well as a food, a beverage, or a food or beverage composition to which said composition or said food additive is added.

Solution to Problem

The composition for promoting absorption of a poorly water-soluble phytochemical according to the present invention comprises a polysaccharide-containing lactic acid bacterial product as an active ingredient, wherein the lactic acid bacterial product is a product produced by *Lactobacillus delbrueckii* ssp. *bulgaricus* OLL1251.

In addition, the food additive, the food or a beverage, or the food or beverage composition according to the present invention comprises the composition for promoting absorption of a poorly water-soluble phytochemical according to the present invention.

In addition, the present invention relates to a method for promoting the intake of a poorly water-soluble phytochemical into a body of a human or an animal, comprising the step of administering or ingesting a polysaccharide-containing lactic acid bacterial product to the human or the animal.

In addition, the present invention relates to a use of a polysaccharide-containing lactic acid bacterial product, for promoting the intake of a poorly water-soluble phytochemical into a body of a human or an animal.

In addition, the present invention relates to a use of a polysaccharide-containing lactic acid bacterial product, for preparing the composition for promoting absorption of a poorly water-soluble phytochemical.

DESCRIPTION OF THE INVENTION

Phytochemicals

Figure 1:
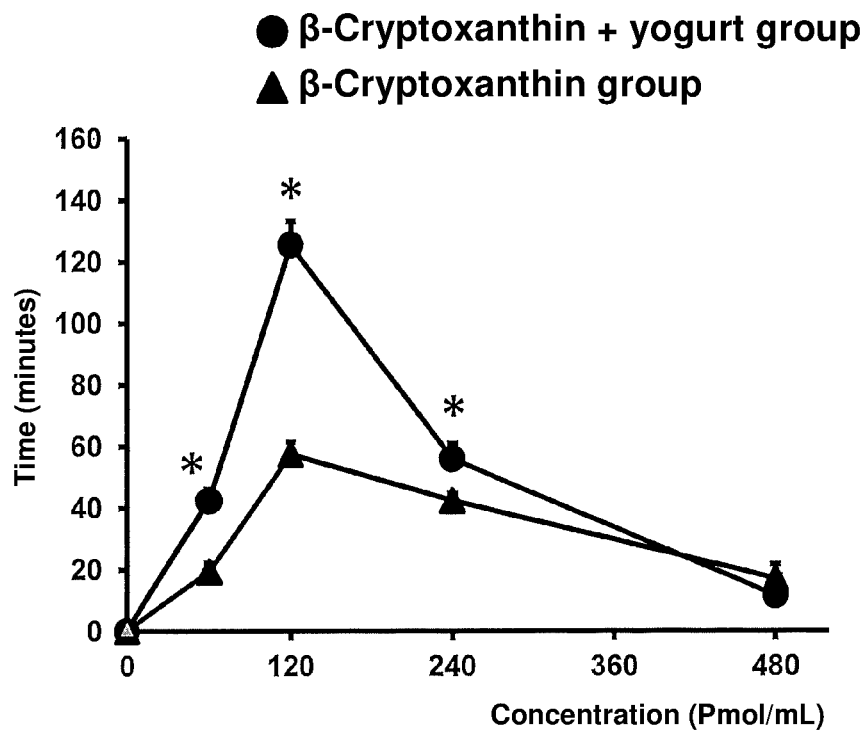
FIG. 1 A graph illustrating a change of a β-cryptoxanthin concentration in a serum when β-cryptoxanthin alone is administered, or β-cryptoxanthin and a yogurt are administered simultaneously, to a rat.

In the present invention, a "phytochemical" means a natural chemical compound present in a plant, a modified body thereof, and a composition containing the compound or the body, wherein the compound, the body, or the composition is administered or is going to be administered as a substance which has a favorable effect on the maintenance or improvement of a health condition but which is not essential to maintain a usual body function. Accordingly, in the present invention, the phytochemical means not only a pure or a somewhat pure compound that is originated from a plant but also a plant-originated composition containing the compound as a main component, or the like, e.g., a fraction of the composition.

According to a preferred aspect of the present invention, the phytochemical means, for example, a polyphenol, an organic sulfur compound, and a terpenoid.

In the present invention, illustrative examples of the preferred polyphenol include flavonoids, diketones and tetraterpene. Specifically, illustrative examples of flavonoids include flavones (for example, apigenin and luteolin), isoflavones (for example, genistein and daidzein), flavonols (for example, quercetin, myricetin, and kaempferol), flavanones (for example, hesperetin and naringenin), flavan-3-ols (for example, catechin and epicatechin), and anthocyanins (for example, cyanidin and delphinidin). Curcumin may be mentioned as a specific example of the diketones.

Illustrative examples of the preferred organic sulfur compound include isothiocyanates (for example, sulforaphane), cysteine sulfoxides (for example, methylcysteine sulfoxide), and sulfines (for example, allicin).

Tetraterpene may be mentioned as the terpenoid. Specifically, illustrative examples thereof include carotenoids (for example, β-carotene, α-carotene, β-cryptoxanthin, lycopene, lutein, capsanthin, and astaxanthin).

In the present invention, phytochemicals include analogues of the compounds mentioned above. Illustrative examples of the preferred analogues include: in the case of genistein, its glucoside (genistin) and conjugates (glucuronic acid conjugate and sulfuric acid conjugate); in the case of quercetin, its methylated body (Isorhamnetin), glucosides (rutin and quercetin glucoside), and conjugates (glucuronic acid conjugate and sulfuric acid conjugate); in the case of kaempferol, its glucoside (hesperidin) and conjugates (glucuronic acid conjugate and sulfuric acid conjugate); in the case of epicatechin and catechin, their isomers (catechin), polymers (procyanidin B1, procyanidin B2, procyanidin B5, procyanidin C1, and so forth), conjugates (glucuronic acid conjugate and sulfuric acid conjugate), and gallic acid esters (epicatechin gallate and epigallocatechin gallate); in the case of hesperetin, its glucoside (hesperidin) and conjugates (glucuronic acid conjugate and sulfuric acid conjugate); in the case of naringenin, its glucosides (kaempferol and astragalin) and conjugates (glucuronic acid conjugate and sulfuric acid conjugate); in the case of β-carotene, its isomers (α-carotene and γ-carotene) and metabolites (retinol palmitate, apo-10-carotenal, and retinol); and in the case of lycopene, its metabolite (apo-10-ricopenal).

In addition, in the present invention, phytochemicals include extracted and concentrated products that are originated from a plant. Preferred examples thereof include: in the case of genistein, extracted and concentrated products originated from a soy bean, a red bean, a green pea, and a broad bean; in the case of quercetin, extracted and concentrated products originated from an onion and an apple; in the case of kaempferol, extracted and concentrated products originated from a tea and a broccoli; in the case of epicatechin and catechin, extracted and concentrated products originated from a cacao bean and a tea; in the case of hesperetin, extracted and concentrated products originated from a mandarin orange; in the case of naringenin, extracted and concentrated products originated from a grapefruit and an orange; in the case of luteolin, extracted and concentrated products originated from a wild sesame, a *perilla*, a crown daisy, and a green pepper; in the case of epicatechin, extracted and concentrated products originated from a cacao bean; in the case of β-carotene, extracted and concentrated products originated from a carrot and a spinach; in the case of α-carotene, extracted and concentrated products originated from a carrot; in the case of lycopene, extracted and concentrated products originated from a tomato; in the case of lutein, extracted and concentrated products originated from a yellow carrot, a spinach, and a marigold; and in the case of capsanthin, extracted and concentrated products originated from a bell pepper and a green pepper.

In the present invention, the phytochemical is poorly water-soluble. According to the preferred aspect of the present invention, a poorly water-soluble phytochemical is the one having the dissolution rate in water of 88% or less, preferably 50% or less, more preferably 20% or less, the most preferably 1% or less. In the present invention, the "dissolution rate" is an index indicating dissolvability of a compound into water, and is also represented by the value, in terms of the percentage (%), obtained by dividing a concentration (w/v) of the compound in a supernatant, which is obtained by shaking the compound in pure water to dissolve the compound therein and by centrifuging the solution, by a concentration (w/v) of the compound in pure water before being dissolved therein. The concentration may be measured by using a spectrophotometer. In the present invention, preferably, a solution prepared by adding 33.3 mg of a phytochemical compound into 10 mL of pure water is used for the measurement of the "dissolution rate" When a more poorly water-soluble phytochemical is used, the "dissolution rate" may be measured by using a solution that is prepared by adding 3.3 mg of a phytochemical compound into 10 mL of pure water. The temperature condition in the measurement of the "dissolution rate" is set to 21±2° C. Alternatively, poor water solubility of the phytochemical may be expressed, as an index, by "a concentration (w/v) of the compound in a supernatant, which is obtained by shaking the compound in pure water to dissolve the compound therein and by centrifuging the solution"; in this case, the dissolution rate of 88% or less corresponds to 293 mg/100 g or less. In the present invention, it is considered that the phytochemical to be promotingly absorbed is not necessarily in a condition of being dissolved in water. Namely, it is considered that the effect of promoting absorption of the phytochemical exhibited by the present invention can be also obtained when the phytochemical is ingested in a solid condition or in a condition of being suspended in water.

Composition for Promoting Absorption

In the present invention, promoting absorption of a phytochemical means that the intake of the phytochemical into a body, in particular, a migration speed and/or a migration amount of the phytochemical into a blood is significantly increased, in comparison with a reference in which the phytochemical is ingested without a polysaccharide-containing lactic acid bacterial product. Specifically, promoting absorption of a phytochemical means that, after the composition is administered, a higher blood concentration is obtained in comparison with the reference, and/or, a larger Area Under the blood concentration-time Curve (AUC) is obtained in comparison with the reference. This allows not only obtaining an effect of ingesting the phytochemical with a smaller quantity or a shorter time, but also reducing costs for a raw material(s). Furthermore, adding the composition for promoting absorption of phytochemical according to the present invention to a food, or a beverage, or a food or beverage composition can enhance an added value of the food or beverage or the like, and thereby also can enhance a commercial value of the same.

Polysaccharide-Containing Lactic Acid Bacterial Product

In the present invention, a polysaccharide-containing "lactic acid bacterial product" widely means not only a product fermented with a lactic acid bacterium, but also a composition that is supposed to contain a polysaccharide, as a result of fermentation using a lactic acid bacterium, such as a cultured product with a lactic acid bacterium and a lactic acid bacterial metabolite.

In the present specification. "polysaccharide" is a saccharide-chained polymer formed of saccharides such as galactose, glucose, rhamnose, mannose, and N-acetyl glucosamine. The polysaccharide may include a neutral polysaccharide and/or an acidic polysaccharide bound to a phosphoric acid group. The molecular weight thereof is usually in the range of 5,000 to 500,000.

In the present invention, a product produced by *Lactobacillus delbrueckii* ssp. *bulgaricus* OLL1251 (which may be hereinafter abbreviated as "*Lactobacillus bulgaricus* OLL1251", or "OLL1251") is used, as the "lactic acid bacterial product". The "lactic acid bacterial product" produced by OLL1251 has a superior action of promoting absorption of phytochemical in comparison to a product produced by analogous strains.

According to a preferred aspect of the present invention, it is preferable to use the "lactic acid bacterial product" produced by a combination of OLL1251 and *Streptococcus thermophilus* OLS3290 (which may be hereinafter abbreviated as "OLS3290"). The combination of OLL1251 and OLS3290 can obtain merits of efficiently producing the "lactic acid bacterial product", in particular, of obtaining the "lactic acid bacterial product" having a superior action of promoting absorption of the phytochemical in a short fermentation time.

In accordance with the Budapest Treaty, *Lactobacillus delbrueckii* ssp. *bulgaricus* OLL1251 described above is internationally deposited to the National Institute of Technology and Evaluation, Patent Microorganisms Depositary Center (#122, 2-5-8 Kazusakamatari, Kisarazu-shi, Chiba, Japan) with the deposition date of 25 Apr. 2018 and as the deposition number of NITE BP-02703.

Also, in accordance with the Budapest Treaty, *Streptococcus thermophilus* OLS3290 is internationally deposited to the National Institute of Technology and Evaluation, Patent Microorganisms Depositary Center with the deposition date of 19 Jan. 2004 and as the deposition number of FERM BP-19638.

In this specification, the "product fermented with a lactic acid bacterium" means: a cultured product obtained by fermentation with the lactic acid bacterium, *Lactobacillus delbrueckii* ssp. *bulgaricus* OLL1251, or, as the preferred aspect, with a combination of *Lactobacillus delbrueckii* ssp. *bulgaricus* OLL1251 and *Streptococcus thermophilus* OLS3290; and a composition including the cultured product; and a composition obtained by processing the composition. Accordingly, the product fermented with a lactic acid bacterium includes a product fermented with *Lactobacillus delbrueckii* ssp. *bulgaricus* OLL1251 or with a combination of *Lactobacillus delbrueckii* ssp. *bulgaricus* OLL1251 and *Streptococcus thermophilus* OLS3290, as well as a product obtained by processing said fermented product. Illustrative examples of the processed product include: a filtrated solution or a supernatant solution of the cultured product that are obtained by sterilizing the cultured product (the product fermented with a lactic acid bacterium) using, for example, filtration, centrifugation, or membrane separation; a concentrated product obtained, using an evaporator or the like, from said filtrated solution or supernatant solution, or product fermented with a lactic acid bacterium, or the like; a pasted product of the fermented product; a diluted product of the fermented product; and a dried product of the fermented product (obtained by, for example, freeze-drying, heat-drying, or decompression-drying). The processing may be carried out by any one of or a combination of a plurality of said processes such as treatments of sterilization (for example, filtration, centrifugation, and membrane separation), precipitation, concentration, pasting, dilution, and drying. Here, illustrative examples of culture media include a defatted milk powder culture medium to which a yeast extract is added and an MRS culture medium.

According to a preferred aspect of the present invention, the lactic acid bacterial product is especially preferably a fermented milk product, a cultured milk product, or a milk metabolite, which is produced by the lactic acid bacterium, *Lactobacillus delbrueckii* ssp. *bulgaricus* OLL1251, or by a combination of *Lactobacillus delbrueckii* ssp. *bulgaricus* OLL1251 and *Streptococcus thermophilus* OLS3290. Fermented milk (yogurt) may be mentioned as an example of the fermented milk product, the cultured milk product, or the milk metabolite. In the present invention, the fermented milk (yogurt) may be preferably a supernatant thereof. To the fermented milk, a defatted powder milk and a culture solution such as a decomposed product of whey, as well as a thickener or a gelling agent, such as pectin, guar gum, xanthan gum, carrageenan, processed starch may be added.

In the present invention, illustrative examples of milk include animal milk such as cow milk and a processed product thereof (for example, defatted milk, whole milk powder, defatted milk powder, condensed milk, casein, whey, fresh cream, compound cream, butter, butter milk powder, and cheese), and plant milk such as soybean milk originated from soybeans. The milk may be sterilized or not be sterilized.

According to an aspect of the present invention, a so-called raw material admixture for fermented milk may be used as the raw material for fermented milk (yogurt). The raw material admixture for fermented milk is a mixture containing raw material milk and other ingredients. The raw material admixture for fermented milk may be obtained by dissolving, on heating, raw materials that are normally used to produce the fermented milk, such as, raw material milk, water, and other optional ingredients (for example, sugar, carbohydrate, sweetener, acidulant, mineral, vitamin, and fragrance), and thereafter by mixing the raw materials thus dissolved. The raw material milk may include water, raw milk, sterilized milk, defatted milk, powdered whole milk, powdered defatted milk, concentrated whole milk, concentrated defatted milk, butter milk, butter, cream, cheese, and the like. The raw material milk may include whey protein concentrate (WPC), whey protein isolate (WPI), α-lactalbumin (α-La), β-lactoglobulin (β-Lg), and the like.

In the present invention, fermented milk (yogurt) may be prepared by the conventional methods in the art. Namely, fermented milk (yogurt) may be prepared via steps: such as a preparation step of a raw material admixture, a (heat-)sterilization step of the raw material admixture, a cooling step of the raw material admixture, an adding step of a starter, a fermentation step, and a cooling step of fermented milk. In these steps, normal conditions used for production of fermented milk (yogurt) may be used as appropriate, preferably, the (heat-)sterilization step of the raw material admixture, the cooling step of the raw material admixture, the adding step of a starter, the fermentation step, and the cooling step of fermented milk are carried out, in this order.

In the present invention, a culture medium usually used for culturing a lactic acid bacterium in the art may be used, as a culture medium for culturing the lactic acid bacterium, *Lactobacillus delbrueckii* ssp. *bulgaricus* OLL1251, or a combination of *Lactobacillus delbrueckii* ssp. *bulgaricus* OLL1251 and *Streptococcus thermophilus* OLS3290. Namely, any culture medium may be used so far as the culture medium properly contains a main carbon source as well as a nitrogen source, an inorganic substance and other nutrients. As the carbon source, lactose, glucose, sucrose, fructose, starch hydrolysate, molasses and the like may be used in accordance with assimilation of a strain to be used. As the nitrogen source, nitrogen-containing organic substances such as casein hydrolysate, whey protein hydrolysate, α-lactoalbumin, β-lactoglobulin, glycomacropeptide, and soybean protein hydrolysate. In addition, meat extract, fish extract, yeast extract, or the like may be used, as a growth promoter.

In the present invention, the lactic acid bacterium, *Lactobacillus delbrueckii* ssp. *bulgaricus* OLL1251, or a combination of *Lactobacillus delbrueckii* ssp. *bulgaricus* OLL1251 and *Streptococcus thermophilus* OLS3290 may be cultured under an anaerobic condition, or under a slightly aerobic condition that is used in liquid static culturing and the like. As the culturing method under an anaerobic condition, a known culturing method such as one under a carbon gas phase may be used, or another method may be used, too. In general, the culturing temperature is preferably in the range of 30° C. or more to 47° C. or less, more preferably in the range of 35° C. or more to 46° C. or less, still more preferably in the range of 37° C. or more to 45° C. or less.

The pH of the culture medium during culturing of the lactic acid bacterium is kept preferably in the range of 6 or more to 7 or less; but may be in another range so far as the bacterium can be grown. Usually, the culturing time of the lactic acid bacterium and the like is preferably in the range of 1 hour or more to 48 hours or less, more preferably in the range of 1.5 hours or more to 36 hours or less, still more preferably in the range of 2 hours or more to 24 hours or less.

According to an aspect of the present invention, fermented milk (yogurt) typically has a milk solids-not-fat concentration of 8% by weight or more, and also has the number of lactic acid bacterium or the number of yeast in the range of $10^6$/mL or more to $10^{11}$/mL or less.

Components of the Composition for Promoting Absorption of Phytochemical, as Well as Form and Optional Ingredient of Said Composition In the present invention, as the "composition for promoting absorption", the "lactic acid bacterial product" may be used as it is in the form of a fermented product, a cultured product, a metabolite, or the like, which is produced by the lactic acid bacterium, *Lactobacillus delbrueckii* ssp. *bulgaricus* OLL1251, or a combination of *Lactobacillus delbrueckii* ssp. *bulgaricus* OLL1251 and *Streptococcus thermophilus* OLS3290. It is preferable that the composition for promoting absorption is used in its pharmaceutically formulated form. Therefore, in the present invention, the "composition for promoting absorption" includes, for example, not only a pharmaceutical but also those supplied in a form as they are, or preferably those supplied in a form of formulation orally ingested, i.e., in a form of a so-called supplement. Also, the composition for promoting absorption includes those added, as food additives, to other food, or other food or beverage, thereby providing the food, or the food or beverage with an action of promoting absorption of phytochemical.

In addition, according to the present invention, a food or a beverage comprising the composition for promoting absorption of phytochemical according to the present invention; the food or the beverage processed: and the food or beverage composition are also encompassed in the present invention.

In the present invention, a formulation is prepared by a usual method concurrently using an additive acceptable for formularization. The formulation is preferably prepared as an oral formulation. The formulation may be in a form of a solid formulation such as a tablet, a powder, a fine granule, a granule, a capsule, a pill, and a sustained release agent; or in the form of liquid formulation such as a solution, a suspension, and an emulsion. Illustrative examples of the additive acceptable for formularization include an excipient, a stabilizer, a preservative, a wetting agent, an emulsifier, a lubricating agent, a sweetener, a colorant, a fragrance, a buffering agent, an antioxidant, and a pH-adjusting agent. Specifically, illustrative examples of the food additive include seasonings such as a processed seasoning, a flavor seasoning, and a seasoning admixture.

In the present invention, a food, or a beverage, and a food or beverage composition may be those processed so that a human or an animal can eat or drink them, and may be in orally ingestible form such as a solution, a suspension, an emulsion, a powder, or a molded solid agent, but are not limited to the above. Specifically, illustrated examples of the food or the beverage, and the food or beverage composition include milk products such as a milk beverage (including processed milk), a yogurt, a lactic acid bacterium beverage, a fermented milk, an ice cream, a cream, and a cheese: beverages such as a refreshing beverage, a fruit drink, a vegetable drink, a soybean drink, a coffee drink, a tea drink, a jelly drink, an energy drink, a beauty drink, cocoa, a powdered drink such as smoothie, a powdered sports drink, a nutrient-reinforcing powdered drink, a powdered beauty food, a powdered soup, a source of steamed bread, a concentrated drink, and an alcoholic drink; wheat products such as a bread, a pasta, a noodle, a cake admixture, a frying powder, and a bread powder: sweets such as a chocolate, a gum, a candy, a cookie, a gummi, a snack, a Japanese sweet, jerry, and a dessert cake such as a purine; retort foods such as a curry, a pasta source, a pot-au-feu, a stew, and a Japanese food; fats such as a processed fat, a butter, a margarine, a spread, and mayonnaise; instant foods such as a freeze-dried food; processed agricultural products such as a canned agricultural product, a jam/marmalade, a pickle, a boiled bean, a cereal, and a rice porridge; processed marine products; processed animal products; frozen foods such as a pizza, a rice casserole, a gratin, a side dish, and a fried food; and a fluid food, a semi-fluid food, an animal feed, a tablet, and an oral care cosmetic.

In the present invention, the food, or a beverage, and the food or beverage composition also include those classified as a functional food, a health and nutrition food, a health food, a food for specified health use, a food with functional claims, a nutrition functional food, a patient food, a formulated milk powder for a baby, a powdered milk for a pregnant or for a lactating mother, a food or beverage with a note of a reduced disease risk, and the like. The note of a reduced disease risk is a note which indicates that the food or a beverage is capable of reducing a disease risk, and also is determined or recognized on the basis of or with reference to the criteria determined by the FAO-WHO Codex Alimentarius Committee (Codex Committee).

In the present invention, to the food, or a beverage, and the food or beverage composition, an optional ingredient may be added, as needed. The optional ingredient includes those usually blended in a food or a beverage: for example, a sweetener; an acidulant; a juice or an extract of a vegetable, a fruit and a seed; nutritional elements such as a vitamin, a mineral, and an amino acid; a lactic acid bacteria (except for the essential lactic acid bacterium according to the embodiment of the present invention), useful microorganisms such as a *Bifidobacterium* and a propionic acid bacterium, and their fermented products; functional carbohydrates such as an oligosaccharide; existing functional stuff such as royal jerry, glucosamine, astaxanthin, collagen, and polyphenol; and a flagrance, a pH adjusting agent, an excipient, an acidulant, a colorant, an emulsifier, and a preservative.

As can be dearly seen in the above description, according to an aspect of the present invention, provided is a use of the polysaccharide-containing lactic acid bacterial product for producing the composition for promoting absorption of a poorly water-soluble phytochemical according to the present invention.

Method for Ingesting the Composition for Promoting Absorption of Phytochemical

In the present invention, the ingesting amount of the composition for promoting absorption of phytochemical may be determined as appropriate. According to an aspect of the present invention, the ingesting amount of the composition corresponds to the ingesting amount of the polysaccharide in the range of about 200 μg or more/day, preferably in the range of 200 μg/day or more to 60,000 μg/day or less, more preferably in the range of 300 μg/day or more to 45,000 μg/day or less, still more preferably in the range of 400 μg/day or more to 30,000 μg/day or less, the most preferably in the range of 500 μg/day or more to 15,000 μg/day or less. (The expression "mass/day or more" is equivalent to the expression "mass or more/day", and the expression "mass/day or less" is equivalent to the expression "mass or less/day.") The ingesting time is not particularly limited. For example, it is preferable that the composition is orally ingested at least one time or more.

According to another aspect of the present invention, a necessary administering amount obtained from animal testing (for example, mouse testing) may be converted to a necessary administering amount for a human body by using the following formula based on the written material of the Food Safety Commission.

[A necessary administering amount to human body (converted value)]=[A necessary administering amount to animal]×[Lower limit of woman's body weight: 40 kg]÷[safety coefficient: 100]

As can be clearly seen in the above description, according to an aspect of the present invention, provided is a method for promoting the intake of a poorly water-soluble phytochemical into a body of a human or an animal, comprising the steps of administering or ingesting a polysaccharide-containing lactic acid bacterial product to the human or the animal. According to another aspect of the present invention, provided is a use of a polysaccharide-containing lactic acid bacterial product for promoting the intake of a poorly water-soluble phytochemical into a body of a human or an animal.

EXAMPLES

In Examples described below, the following strains were used for comparison.

*Lactobacillus delbrueckii* ssp. *bulgaricus* OLL1247

In accordance with the Budapest Treaty, this strain is internationally deposited to the National Institute of Technology and Evaluation, Patent Microorganisms Depositary Center (#122, 2-5-8 Kazusakamatari, Kisarazu-shi, Chiba, Japan) with the deposition date of Jun. 3, 2014 and as the deposition number of NITE BP-01814.

*Lactobacillus delbrueckii* ssp. *bulgaricus* OLL1224

In accordance with the Budapest Treaty, this strain is internationally deposited to the National Institute of Technology and Evaluation, Patent Microorganisms Depositary Center with the deposition date of Feb. 7, 2009 and as the deposition number of NITE BP-778.

*Streptococcus thermophilus* OLS3078

In accordance with the Budapest Treaty, this strain is internationally deposited to the National Institute of Technology and Evaluation, Patent Microorganisms Depositary Center with the deposition date of 23 Aug. 2013 and as the deposition number of NITE BP-01697.

In Examples described below, the following measurement methods were commonly used.

Measurement of Polysaccharide Content in Yogurt

Content of the polysaccharide in a yogurt was measured in accordance with a phenol sulfuric acid method (Hodge, et al., "Methods in Carbohydrate Chemistry". Vol. 1, p. 338 (1962)). Specifically, the method is as follows.

Firstly, 1 g of trichloroacetic acid was added to 10 g of yogurt, and then, they were thoroughly stirred. Next, the trichloroacetic acid-added yogurt was centrifuged under the conditions: at 10,000 rpm for 10 minutes at 4° C., and then, a supernatant thus obtained was transferred to a different tube. Next, ethanol 99.5% the amount of which is twice as much as the supernatant was added to the supernatant. Then, when the ethanol-added supernatant was statically left overnight in a refrigerator, a precipitate was formed in the tube. The precipitate was centrifuged under the condition: at 10,000 rpm for 10 minutes at 4° C., and thereafter, 3 mL of ultrapure water was added to the precipitate thus obtained to prepare a polysaccharide extract solution. Then, 500 µL of a phenol reagent (5% (w/v)) was added to 500 µL of the polysaccharide extract solution, and then, the resulting mixture solution was stirred. Immediately after 2.5 mL of concentrated sulfuric acid was added to the mixture solution, and the resulting mixture solution was stirred for 10 seconds. Then, the mixture solution was statically left for 20 minutes or more at room temperature, the absorbance of the mixture solution at 490 nm was measured with a spectrophotometer. The reference solution was prepared as described below, and the absorbance thereof at 490 nm was measured in a similar manner to the above. In preparation of the reference solution, 500 µL of the phenol reagent (5% (w/v)) was added to 500 µL of a standard glucose solution, followed by stirring the resulting mixture solution. Immediately after 2.5 mL of concentrated sulfuric acid was added to the mixture solution, and the resulting mixture solution was stirred for 10 seconds. Then, the mixture solution was left statically for 20 minutes or more at room temperature.

Measurement of Quercetin Metabolites

A quercetin conjugate and an isorhamnetin conjugate, which are quercetin metabolites, were measured as follows. 45 uL of a glucuronidase solution (10,000 U/mL; manufactured by Sigma-Aldrich Corp.) dissolved in a 0.1 M sodium acetate buffer solution (pH 5.0), and 5 µL of a 0.1 M ascorbic acid solution dissolved in a 0.1 M sodium acetate buffer solution (pH 5.0) were added to 50 µL of a serum; and then, the resulting mixture was warmed at 37° C. for 2 hours. Then, 300 µL of methanol was added to the mixture to terminate the enzymatic reaction, and the mixture was centrifuged (at 12,000 rpm for 10 minutes at 4° C.). The supernatant thus obtained was transferred to a different tube, and then, the solvent was removed by centrifugal concentration. The resulting product was dissolved into 300 µL of a 50% acetonitrile solution containing 0.1% formic acid to prepare a sample for HPLC.

For the HPLC measurement, Nexera XR (manufacture by Shimadzu Corp.) was used. As a MS/MS detector, 4500 QTRAP (manufactured by Sciex Pte. Ltd.) was used. As a column, ACQUITY UPLC HSS T3, 1.8 µm (2.1×50 mm) (manufactured by Waters Corp.) was used. Column temperature was set at 40° C. As for the mobile phase, a 0.1% formic acid solution was prepared as an A solution, and an acetonitrile solution containing 0.1% formic acid was prepared as a B solution. The column was kept with 30% of the B solution for 1 minute, and then, the concentration gradient of B solution was gradually changed up to 45% during a period of 4.5 minutes to elute a target substance. Then, the column was washed with 99% B solution for 2 minutes, and was kept with 30% B solution for 3 minutes. The flow rate was set to 0.3 mL/minute. The MS/MS analysis was carried out with an ESI negative mode. The MS/MS analysis was carried out under the following condition: a curtain gas flow rate of 30 psi; a collision gas flow rate of 9 psi; an ion spray voltage of −4500 V; a turbo gas temperature of 600° C., and an ion source gas of 70 psi.

Measurement of β-Carotene

90 µL of a physiological salt solution and 300 µL of a dichloromethane-methanol solution (dichloromethane:methanol=1:2) were added to 50 µL of a serum. Next, 150 µL of hexane was further added to the resulting solution to extract A-carotene. The upper layer of the solution was transferred to a different tube, and then, the solvent was removed by nitrogen reflux. Then, the resulting product was dissolved into 150 µL of an ethyl acetate-methanol solution (ethyl acetate:methanol=30:70) containing 0.1% ammonium acetate to obtain an sample for HPLC.

For the HPLC measurement, the 1200 series (manufacture by Agilent Technologies, Inc.) was used. TSKgel ODS-80 TsQA (5.0×250 mm) (manufactured by Tosoh Corp.) was used as a column. Column temperature was set at 40° C. An ethyl acetate-methanol solution (ethyl acetate:methanol=30:70) containing 0.1% ammonium acetate was prepared as a mobile phase. The flow rate was set to 0.3 mL/minute, and the absorbance at the wavelength of 450 nm was measured.

Evaluation for Dissolvability of Phytochemical (1) Experimental Method

Epicatechin (manufactured by Sigma-Aldrich Corp.), catechin (manufactured by Tokyo Chemical Industry Co., Ltd.), quercetin (manufactured by Wako Pure Chemical Industries, Ltd.), genistein (manufactured by Tokyo Chemical Industry Co., Ltd.), rutin (manufactured by Wako Pure Chemical Industries, Ltd.), α-glucosyl rutin (manufactured by Wako Pure Chemical Industries, Ltd.), hesperidin (manufactured by Wako Pure Chemical Industries, Ltd.), naringin (manufactured by Sigma-Aldrich Corp.), naringenin (manufactured by Sigma-Aldrich Corp.), kaempferol (manufactured by Extra Synthase Inc.), β-carotene (manufactured by Wako Pure Chemical Industries, Ltd.), β-cryptoxanthin (manufactured by Wako Pure Chemical Industries, Ltd.), capsanthin (manufactured by Tokyo Chemical Industry Co., Ltd.), lycopene (manufactured by Wako Pure Chemical Industries, Ltd.), and luteolin (manufactured by Tokyo Chemical Industry Co., Ltd.) were used. In accordance with the administering amount used in Examples, 33.3 mg of each of epicatechin, catechin, quercetin, genistein, naringenin, kaempferol, and luteolin was added to 10 mL of ultrapure water. Furthermore, 10 mL of ultrapure water was added to the glucoside phytochemical such that the amount of aglycone (portion other than carbohydrate obtained by hydrolysis of glucoside) can be equal to 33.3 mg; namely, 67.3 mg of rutin (33.3 mg of quercetin); 89.6 mg of α-glucosyl rutin (33.3 mg of quercetin); 67.3 mg of hesperidin (33.3 mg of hesperetin); or 71.0 mg of naringin (33.3 mg of naringenin). As for the terpenoids, in accordance with the administering amount used in Experiments, 10 mL of ultrapure water was added to 3.3 mg of each of β-carotene and lycopene. The solutions thus prepared were shaken for 3 hours, and then, were centrifuged at 2000×g for 10 minutes. The centrifuged supernatants were filtrated by using a 0.45 µL filter. The absorbance of the centrifuged supernatants were measured by using a spectrophotometer (at 280 nm in the cases of epicatechin, catechin, hesperidin, naringin, naringenin, and luteolin; at 260 nm in the case of genistein; at 360 nm in the cases of quercetin, rutin, G-glucosyl rutin, and kaempferol; at 450 nm in the cases of β-carotene, α-carotene, and β-cryptoxanthin; and at 470 nm in the cases of lycopene and capsanthin). Each compound was dissolved in 80% methanol or methanol to obtain a calibration curve; and then, the concentration of the centrifuged supernatant was obtained. A series of the operations above were carried out under the temperature condition of 21±2° C. The dissolution rate was calculated in accordance with the following formula.

Dissolution rate (%)=[(concentration of the centrifuged supernatant after dissolution by shaking (w/v))÷(concentration of the solution before dissolution by shaking (w/v)]×100

(2) Results

Results are shown in Table 1. Catechin and α-glucosyl-rutin had the dissolution rate of 89% or more; and thus, they were water-soluble phytochemicals. On the other hand, epicatechin, genistein, quercetin, rutin, kaempferol, hesperidin, naringin, naringenin, β-carotene, α-carotene, lycopene, luteolin, β-cryptoxanthin, and capsanthin had the dissolution rate of 88% or less; and thus, they were poorly water-soluble. These results indicate that in the poorly water-soluble phytochemicals having the dissolution rate of 88% or less, ingesting the polysaccharide-containing lactic acid bacterial product promotes absorption of the phytochemicals. Here, "concentration (w/v) of the centrifuged supernatant after dissolution by shaking" that is obtained in the measurement of the dissolution rate is called "saturated solubility", and this is described in Table 1. The value of the glucoside phytochemical is described in terms of that of the corresponding aglycone.

TABLE 1

Dissolution rates of phytochemicals

| Compound Group | Compound | Dissolution rate | Saturated solubility mg/100 g |
|---|---|---|---|
| Flavan-3-ol | Catechin | 97% | 323 |
| | Epicatechin | 86% | 287 |
| Isoflavone | Genistein | 0.2% | 0.6 |
| Flavonol | Quercetin | 0.1% or less | 0.1 |
| | Rutin | 0.3% | 1.0 |
| | α-Glucosyl rutin | 89% | 295 |
| | Kaempferol | 0.1% or less | 0.1 |
| Flavanone | Hesperidin | 0.2% | 0.5 |
| | Naringin | 17% | 55 |
| | Naringenin | 0.3% | 1.1 |
| Tetraterpene | β-Carotene | 0.1% or less | 0.1 or less |
| | α-Carotene | 0.1% or less | 0.1 or less |
| | β-Cryptoxanthin | 0.1% or less | 0.1 or less |
| | Capsanthin | 0.1% or less | 0.1 or less |
| | Lutein | 0.1% or less | 0.1 or less |
| | Lycopene | 0.1% or less | 0.1 or less |
| Flavone | Luteolin | 0.1% or less | 0.1 or less |

Experiment 1: Promoting Absorption of β-Carotene (Comparison of OLL1251 with Oilier Strains)

(1) Preparation of Yogurt

*Lactobacillus delbrueckii* ssp. *bulgaricus* OLL1251, *Lactobacillus delbrueckii* ssp. *bulgaricus* OLL1224, and *Lactobacillus delbrueckii* ssp. *bulgaricus* OLL1247 each were applied to a culture medium containing 10% by mass of defatted powdered milk and 0.5 mM of sodium formate, and then, the culture medium was fermented on heating at 43° C. until its pH reached 4.6. The yogurts thus obtained contained 136 μg/g, 88 μg/g, and 68 μg/g of the polysaccharide, respectively.

(2) Experimental Method 32 rats (SD, male, 8 weeks old. Japan SLC, Inc.) were acclimated for 7 days, and then, they were divided into the groups each having 8 rats. They were fasted for 16 hours, and then, β-carotene, a mixture of β-carotene and the yogurt (*Lactobacillus bulgaricus* OLL1251), a mixture of β-carotene and the yogurt (*Lactobacillus bulgaricus* OLL1224), and a mixture of β-carotene and the yogurt (*Lactobacillus bulgaricus* OLL1247) each were administered to the rats of each group. Here, 5 mg/kg-body weight of β-carotene and 11.3 g/kg-body weight of the yogurt were administered. Blood sample was taken from a tail vein before the administration, as well as at 60 minutes, at 120 minutes, at 240 minutes, and at 480 minutes after the administration to obtain respective serums. The β-carotene concentrations in the respective serums were measured in accordance with the method described above.

Hereinafter, the rat group to which β-carotene was administered (control) is called "β-carotene group"; the rat group to which the mixture of β-carotene and the yogurt (*Lactobacillus bulgaricus* OLL1251) was administered (Example) is called "β-carotene+OLL1251 group"; the rat group to which the mixture of β-carotene and the yogurt (*Lactobacillus bulgaricus* OLL1224) was administered (Comparative Example) is called "β-carotene+OLL1224 group"; and the rat group to which the mixture of β-carotene and the yogurt (*Lactobacillus bulgaricus* OLL1247) was administered (Comparative Example) Is called "β-carotene+OLL1247 group."

(3) Results

Results are shown in Table 2. The area under the blood concentration-time curve (AUC) was significantly increased in all of the β-carotene+OLL1251 group, the β-carotene+OLL1224 group, and the β-carotene+OLL1247 group in comparison with the β-carotene group. These results indicate that the ingestion of the yogurt can promote absorption of β-carotene.

TABLE 2

Area Under the blood concentration-time Curve (AUC) of β-carotene

| | β-Carotene (ng · min/mL) |
|---|---|
| β-Caroiene group | 4,502 ± 1,014 |
| β-Carotene + OLL1251 group | 31,814 ± 4,293* |
| β-Carotene + OLL1224 group | 25,771 ± 5,175* |
| β-Carotene + OLL1247 group | 24,375 ± 3,182* |

Average value ± standard deviation
*P < 0.05: there are significant differences relative to the β-carotene group Experiment 2: Promoting Absorption of β-Carotene (*Streptococcus thermophilus* OLS3290 Alone)

(1) Preparation of Yogurt

*Streptococcus thermophilus* OLS3290 and *Streptococcus thermophilus* OLS3078 each were applied to a culture medium containing 10% by mass of defatted powdered milk and 0.1% by weight of casein peptide (manufactured by DOMO, Inc.), and then, the culture medium was fermented on heating at 43° C. until its pH reached 4.6. The yogurts thus obtained contained 76.3 μg/g and 45.8 μg/g of the polysaccharide, respectively.

(2) Experimental Method 24 rats (SD, male, 8 weeks old, Japan SLC, Inc.) were acclimated for 7 days, and then, they were divided into the groups each having 8 rats. They were fasted for 16 hours, and then, β-carotene, a mixture of β-carotene and the yogurt (*Streptococcus thermophilus* OLS3290), and a mixture of β-carotene and the yogurt (*Streptococcus thermophilus* OLS3078) each were administered to the rats of each group. Here, 5 mg/kg-body weight of β-carotene and 11.3 g/kg-body weight of the yogurt were administered. Blood sample was taken from a tail vein before the administration, as well as at 60 minutes, at 120 minutes, at 240 minutes, and at 480 minutes after the administration to obtain respective serums. The β-carotene concentrations in the respective serums were measured in accordance with the method described above.

Hereinafter, the rat group to which β-carotene was administered (control) is called "β-carotene group"; the rat group to which the mixture of β-carotene and the yogurt (*Streptococcus thermophilus* OLS3290) was administered (Reference Example) is called "β-carotene+OLS3290 group"; and the rat group to which the mixture of β-carotene and the yogurt (*Streptococcus thermophilus* OLS3078) was administered (Reference Example) is called "β-carotene+OLS3078 group."

(3) Results

Results are shown in Table 3. The area under the blood concentration-time curve (AUC) was significantly increased in the β-carotene+OLS3290 group in comparison with the β-carotene group. This result indicates that the ingestion of the yogurt can promote absorption of β-carotene.

TABLE 3

Area Under the blood concentration-time Curve (AUC) of β-carotene

| | β-Carotene (ng · min/mL) |
|---|---|
| β-Carotene group | 6,608 ± 892 |
| β-Carotene + OLS3290 group | 27,263 ± 4,306* |
| β-Carotene + OLS3078 group | 17,416 ± 2,468 |

Average value ± standard deviation
*P < 0.05: there is a significant difference relative to the β-carotene group.

Experiment 3: Promoting Absorption of β-Carotene (Combination of *Lactobacillus bulgaricus* OLL1251 and *Streptococcus thermophilus* OLS3290)

(1) Preparation of Yogurt

A commercially available starter (Caspian sea yogurt, manufactured by Fujicco Co., Ltd.), a combination of *Lactobacillus bulgaricus* OLL1247 and *Streptococcus thermophilus* OLS3078, and a combination of *Lactobacillus bulgaricus* OLL1251 and *Streptococcus thermophilus* OLS3290 each were applied to a culture medium containing 10% by mass of defatted powdered milk, and then, the culture medium was fermented on heating at 43° C. until its pH reached 4.6. The yogurts thus obtained contained 15 μg/g, 54 μg/g, and 67 μg/g of the polysaccharide, respectively.

(2) Experimental Method 32 rats (SD, male, 8 weeks old. Japan SLC. Inc.) were acclimated for 7 days, and then, they were divided into the groups each having 8 rats. They were fasted for 16 hours, and then, β-carotene, a mixture of β-carotene and the yogurt (Caspian sea yogurt), a mixture of β-carotene and the yogurt (*Lactobacillus bulgaricus* OLL1247 and *Streptococcus thermophilus* OLS3078), and a mixture of β-carotene with the yogurt (*Lactobacillus bulgaricus* OLL1251 and *Streptococcus thermophilus* OLS3290) each were administered to the rats of each group. Here, 5 mg/kg-body weight of β-carotene and 11.3 g/kg-body weight of the yogurt were administered. Blood sample was taken from a tail vein before the administration, as well as at 60 minutes, at 120 minutes, at 240 minutes, and at 480 minutes after the administration to obtain respective serums. The β-carotene concentrations in the respective serums were measured in accordance with the method described above.

Hereinafter, the rat group to which β-carotene was administered (control) is called "β-carotene group"; the rat group to which the mixture of β-carotene and the yogurt (Caspian sea yogurt) was administered (Comparative Example) is called "β-carotene+Caspian sea YG group"; the rat group to which the mixture of β-carotene and the yogurt (*Lactobacillus bulgaricus* OLL1247 and *Streptococcus thermophilus* OLS3078) was administered (Comparative Example) is called "β-carotene+OLL1247×OLS3078 group"; and the rat group to which the mixture of β-carotene and the yogurt (*Lactobacillus bulgaricus* OLL1251 and *Streptococcus thermophilus* OLS3290) was administered (Example) is called "β-carotene+OLL1251×OLS3290 group".

(5) Results

Results are shown in Table 4. The area under the blood concentration-time curve (AUC) was significantly increased in the β-carotene+OLL1247×OLS3078 group and the β-carotene+OLL1251×OLS3290 group in comparison with the β-carotene group. These results indicate that the ingestion of the yogurt can promote absorption of β-carotene.

TABLE 4

Area Under the blood concentration-time Curve (AUC) of β-carotene

| | β-Carotene (ng · min/mL) |
|---|---|
| β-Carotene group | 5,326 ± 822 |
| β-Carotene + Caspian sea YG group | 15,050 ± 2,001 |
| β-Carotene + OLL1247 × OLS3078 group | 26,917 ± 4,074* |
| β-Carotene + OLL1251 × OLS3290 group | 31,334 ± 6,119* |

Average value ± standard deviation
* P < 0.05: there are significant differences relative to the β-carotene group.

Experiment 4: Promoting Absorption of Quercetin (Combination of *Lactobacillus bulgaricus* OLL1251 and *Streptococcus thermophilus* OLS32901

(1) Yogurt Used

The yogurts prepared in Experiment 3 were used.

(2) Experimental Method 24 rats (SD, male, 8 weeks old, Japan SLC, Inc.) were acclimated for 7 days, and then, they were divided into the groups each having 8 rats. They were fasted for 16 hours, and then, quercetin, and a mixture of quercetin and the yogurt each were administered to the rats of each group. Here, 50 mg/kg-body weight of quercetin and 11.3 g/kg-body weight of the yogurt were administered. Blood sample was taken from a tail vein before the administration, as well as at 60 minutes, at 120 minutes, at 240 minutes, and at 480 minutes after the administration to obtain respective serums. The concentrations of the quercetin conjugate and the isorhamnetin conjugate, which are quercetin metabolites, in the respective serums were measured in accordance with the method described above.

Hereinafter, the rat group to which quercetin was administered (control) is called "quercetin group"; the rat group to which the mixture of quercetin and the yogurt (*Lactobacillus bulgaricus* OLL1247 and *Streptococcus thermophilus* OLS3078) was administered (Comparative Example) is called "quercetin+OLL1247×OLS3078 group"; and the rat group to which the mixture of quercetin and the yogurt (*Lactobacillus bulgaricus* OLL1251 and *Streptococcus thermophilus* OLS3290) was administered (Example) is called "quercetin+OLL1251×OLS3290 group".

(3) Results

Results are shown in Table 5. The area under the blood concentration-time curve (AUC) of the quercetin conjugate in the quercetin+OLL1247×OLS3078 group and the quercetin+OLL1251×OLS3290 group was significantly increased in comparison with the quercetin group. These results indicate that the fermentation using the lactic acid bacterium can promote absorption of quercetin.

TABLE 5

Area Under the blood concentration-time Curve (AUC) of the quercetin conjugate and the isorhamnetin conjugate

| | Quercetin conjugate (nmol · min/mL) | Isorhamnetin conjugate (nmol · min/mL) |
|---|---|---|
| Quercetin group | 745 ± 23 | 432 ± 13 |
| Quercetin + OLL1247 × OLS3078 group | 1,097 ± 37* | 600 ± 67* |
| Quercetin + OLL1251 × OLS3290 group | 1,191 ± 39* | 719 ± 41* |

Average value + standard deviation
* $P < 0.05$: there are significant differences relative to the quercetin group.

Experiment 5: Promoting Absorption of β-Carotene (Comparison with Other Absorption Promotors)

(1) Preparation of Yogurt-Originated Polysaccharide Concentrate

A part of the yogurt of Experiment 4 (*Lactobacillus bulgaricus* OLL1251 and *Streptococcus thermophilus* OLS3290) was taken; and then, to the supernatant thereof was added ethanol the amount of which was three times as much as the supernatant. The resulting mixture was kept in a frozen state, and thereafter, the supernatant of the mixture was centrifuged to obtain a precipitate. This precipitate was freeze-dried to obtain a polysaccharide concentrate. In 11.3 g of the yogurt, 70 mg of the polysaccharide concentrate was included. Hereinafter, the polysaccharide concentrate obtained is called "lactic acid bacterium-originated polysaccharide concentrate".

(2) Experimental Method 48 rats (SD, male, 8 weeks old, Japan SLC, Inc.) were acclimated for 7 days, and then, they were divided into the groups each having 8 rats. They were fasted for 16 hours, and then, β-carotene, a mixture of β-carotene and the lactic acid bacterium-originated polysaccharide concentrate, a mixture of β-carotene and cyclodextrin (manufactured by CycloChem Co., Ltd.), a mixture of β-carotene and starch (originated from rice) (manufactured by Sigma Corp.), a mixture of β-carotene and pectin (originated from apple) (manufactured by Wako Pure Chemical Industries, Ltd.), and a mixture of β-carotene and indigestible dextrin (manufactured by Matsutani Chemical Industry Co., Ltd.) each were administered to the rats of each group. Here, 5 mg/kg-body weight of β-carotene and 70 mg/kg-body weight of the polysaccharide were administered. Blood sample was taken from a tail vein before the administration, as well as at 60 minutes, at 120 minutes, at 240 minutes, and at 480 minutes after the administration to obtain respective serums.

For an easy-to-understand explanation, hereinafter, the rat group to which β-carotene was administered (control) is called "β-carotene group"; the rat group to which the mixture of β-carotene and the lactic acid bacterium-originated polysaccharide concentrate was administered (Example) is called "β-carotene+lactic acid bacterium-originated polysaccharide concentrate group"; the rat group to which the mixture of β-carotene and cyclodextrin was administered (Comparative Example) is called "β-carotene+cyclodextrin group"; the rat group to which the mixture of β-carotene and starch (originated from rice) was administered (Comparative Example) is called "β-carotene+starch (originated from rice) group"; the rat group to which the mixture of β-carotene and pectin (originated from apple) was administered (Comparative Example) is called "β-carotene+pectin (originated from apple) group"; and the rat group to which the mixture of β-carotene and indigestible dextrin was administered (Comparative Example) is called "β-carotene+indigestible dextrin group".

(5) Results

Results are shown in Table 6. The area under the serum concentration-time curve (AUC) was significantly increased in the β-carotene+lactic acid bacterium-originated polysaccharide concentrate group in comparison with the β-carotene group. On the other hand, the AUC in the β-carotene+cyclodextrin group was significantly decreased in comparison with the β-carotene group. These results indicate that the ingestion of the polysaccharide originated from the lactic acid bacterium can more highly promote absorption of β-carotene than that of other polysaccharides.

TABLE 6

Area Under the blood concentration-time Curve (AUC) of β-carotene

| | β-Carotene (ng · min/mL) |
|---|---|
| β-Carotene group | 7,834 ± 1150 |
| β-Carotene + lactic acid bacterium-originated polysaccharide concentrate group | 14.881 ± 2914*# |
| β-Carotene + cyclodextrin group | 3,483 ± 676* |
| β-Carotene + starch (originated from rice) group | 5,206 ± 391 |
| β-Carotene + pectin (originated from apple) group | 13,545 ± 2205 |
| β-Carotene + indigestible dextrin group | 5,220 ± 804 |

Average value ± standard deviation
* $P < 0.05$: there is significant differences relative to the β-carotene group.
$P < 0.05$: there is a significant difference relative to the cyclodextrin group, the starch (originated from rice) group, and the indigestible dextrin group.

Experiment 6: Promoting Absorption of β-Carotene in Human (Addition to Carrot Juice)

(1) Preparation of Yogurt

*Lactobacillus bulgaricus* OLL1251 and *Streptococcus thermophilus* OLS3290 were applied to a culture medium containing 10% by mass of defatted powdered milk, and then, the culture medium was fermented at 43° C. until its pH reached 4.6.

(2) Experimental Method 5 human subjects were fasted for 12 hours, and then, 180 g of a commercially available carrot juice (containing 11 mg of β-carotene) was ingested into the subjects. At 4 hours after the ingestion, their serums were taken. After one week of wash-out, a mixture of 180 g of said carrot juice and 100 g of the yogurt was ingested into the subjects, and at 4 hours after the ingestion, their serums were taken. On the serums obtained was stacked a physiological salt solution; and immediately thereafter, the serums were ultracentrifuged (at 155,000×g for 30 minutes) to fractionate a chylomicron.

(3) Results

Results are shown in Table 7. Amount of change in plasma A-carotene concentration in the fractionated chylomicron before and after the ingestion of the carrot juice was significantly increased in the carrot juice+yogurt group in comparison with the carrot juice group. This result indicates that in human, fermentation with the lactic acid bacterium promotes absorption of the n-carotene contained in the carrot juice.

TABLE 7

Amount of change in plasma β-carotene concentration in the fractionated chylomicron before and after ingesting carrot juice

| | Amount of change in β-carotene before and after ingestion (Δng/mL) |
|---|---|
| Carrot juice group | 18.7 ± 2.6 |
| Carrot juice + yogurt group | 33.4 ± 7.6* |

Average value ± standard deviation
* P < 0.05: there is a significant difference relative to the carrot juice group.

Experiment 7: Promoting Absorption of Carotenoid in Human (Addition to Vegetable Juice)

(1) Preparation of Yogurt

*Lactobacillus bulgaricus* OLL1251 and *Streptococcus thermophilus* OLS3290 were applied to a culture medium containing 10% by mass of defatted powdered milk, and then, the culture medium was fermented at 40° C. until its pH reached 4.2. In the yogurt thus obtained, 90 μg/g of the polysaccharide was included.

(2) Experimental Method

The test was carried out to 10 male subjects with the age between 20 years old or more and 35 years old or less and with BMI between 18.5 kg/m² or more and 25.0 kg/m² or less. The subjects were fasted for 16 hours, and then, either a beverage containing 100 g of a vegetable juice (including a commercially available spinach puree, a commercially available tomato puree, a commercially available carrot juice, 5 mg of α-carotene, 10 mg of β-carotene, 3 mg of lutein, and 10 mg of lycopene) and 100 g of water, or a beverage containing 100 g of said vegetable juice and 100 g of the yogurt was ingested once into the subjects. After two weeks of wash-out, the beverage that was not ingested in the first ingestion test was ingested once into the subjects. The blood sample was taken before the ingestion of the test food, as well as at 2 hours, at 4 hours, at 6 hours, and at 8 hours after the ingestion to obtain respective plasmas.

For an easy-to-understand explanation, hereinafter, the case that the vegetable juice was ingested (control) is called "vegetable juice group", and the case that the mixture of the vegetable juice and the yogurt was ingested (Example) is called "vegetable juice+yogurt group".

(3) Results

Results are shown in Table 8. The areas under the serum concentration-time curve (AUC) of α-carotene, of β-carotene, of lutein, and of lycopene were significantly increased in the vegetable juice+yogurt group in comparison with the vegetable juice group. This result indicates that in human the yogurt can promote absorption of the carotenoids included in the vegetable juice.

TABLE 8

Area Under the blood concentration-time Curve (AUC) of carotenoids originated from vegetable juice

| | Vegetable juice group | Vegetable juice + yogurt group |
|---|---|---|
| α-Carotene (pmol · hr/mL) | 115 ± 19 | 152 ± 21* |
| β-Carofene (pmol · hr/mL) | 178 ± 32 | 310 ± 64* |

TABLE 8-continued

Area Under the blood concentration-time Curve (AUC) of carotenoids originated from vegetable juice

| | Vegetable juice group | Vegetable juice + yogurt group |
|---|---|---|
| Rutin (pmol · hr/mL) | 42 ± 21 | 81 ± 17* |
| Lycopene (pmol · hr/mL) | 47 ± 23 | 147 ± 37* |

Average value ± standard deviation
* P < 0.05: there are significant differences relative to the vegetable juice group.

Experiment 8: Promoting Absorption of Carotenoid in Human (Addition to Formulation Including β-Carotene and Lycopene)

(1) Yogurt Used

The yogurt prepared in Experiment 7 was used.

(2) Experimental Method

The test was carried out to 9 male subjects with the age between 20 years old or more and 35 years old or less and with BMI between 18.5 kg/m² or more and 25.0 kg/m² or less. The subjects were fasted for 16 hours, and then, either a beverage containing 25 g of a carotenoid formulation (10 mg of n-carotene (manufactured by San-Ei Gen F.F.I., Inc.; New Carotin Base 250) and 10 mg of lycopene (manufactured by Lycored Ltd.: TOMATO-O-Red 2% SG)) and 100 g of water, or a beverage containing 25 g of said carotenoid formulation and 100 g of the yogurt was ingested once into the subjects. After two weeks of wash-out, the beverage that was not ingested in the first ingestion test was ingested once into the subjects. The blood sample was taken before the ingestion of the test food, as well as at 2 hours, at 4 hours, at 6 hours, and at 8 hours after the ingestion to obtain respective plasmas.

For an easy-to-understand explanation, hereinafter, the case that the carotenoid formulation was ingested (control) is called "carotenoid formulation group", and the case that the mixture of the carotenoid formulation and the yogurt was ingested (Example) is called "carotenoid formulation+yogurt group".

(3) Results

Results are shown in Table 9. The areas under the serum concentration-time curve (AUC) of β-carotene and of lycopene were significantly increased in the carotenoid formulation+yogurt group in comparison with the carotenoid formulation group. This result indicates that in human the yogurt can promote absorption of the carotenoids included in the carotenoid formulation.

TABLE 9

Area Under the blood concentration-time Curve (AUC) of carotenoids originated from carotenoid formulation

| | Carotenoid formulation group | Carotenoid formulation + yogurt group |
|---|---|---|
| β-Carotene (pmol · hr/mL) | 314 ± 80 | 812 ± 144* |
| Lycopene (pmol · hr/mL) | 39 ± 44 | 282 ± 54* |

Average value ± standard deviation
* P < 0.05: there are significant differences relative to the carotenoid formulation group.

Experiment 9: Promoting Absorption of β-Cryptoxanthin (1) Yogurt Used

*Lactobacillus bulgaricus* OLL1251 and *Streptococcus thermophilus* OLS3290 were applied to a culture medium containing 10% by mass of defatted powdered milk, and then, the culture medium was fermented on heating at 43° C. until its pH reached 4.2. The yogurt thus obtained contained 105.8 μg/g of the polysaccharide.

(2) Experimental Method 16 rats (SD, male, 8 weeks old, Japan SLC, Inc.) were acclimated for 7 days, and then, they were divided into the groups each having 8 rats. They were fasted for 16 hours, and then, β-cryptoxanthin and a mixture of β-cryptoxanthin and the yogurt each were administered to the rats of each group. Here, 3 mg/kg-body weight of β-cryptoxanthin and 11.3 g/kg-body weight of the yogurt were administered. Blood sample was taken from a tail vein before the administration, as well as at 60 minutes, at 120 minutes, at 240 minutes, and at 480 minutes after the administration to obtain respective serums. For an easy-to-understand explanation, hereinafter, the rat group to which β-cryptoxanthin was administered (control) is called "β-cryptoxanthin group", and the rat group to which the mixture of β-cryptoxanthin and the yogurt was administered (Example) is called "β-cryptoxanthin+yogurt group".

(3) Measurement of β-Cryptoxanthin

90 μL of a physiological salt solution and 300 μL of a dichloromethane-methanol solution (dichloromethane:methanol=1:2) were added to 50 μL of the serum. Next, 150 μL of hexane was further added to the resulting solution to extract β-cryptoxanthin. The upper layer of the solution was transferred to a different tube, and then, the solvent was removed by nitrogen reflux. Then, the resulting product was dissolved into 150 μL of an ethyl acetate-methanol solution (ethyl acetate:methanol=30:70) containing 0.1% ammonium acetate to obtain an sample for HPLC.

(4) Condition of HPLC Analysis

For the HPLC measurement, the 1200 series (manufacture by Agilent Technologies, Inc.) was used. TSKgel ODS-80 TsQA (5.0×250 mm) (manufactured by Tosoh Corp.) was used as a column. Column temperature was set at 40° C. An ethyl acetate-methanol solution (ethyl acetate:methanol=30:70) containing 0.1% ammonium acetate was prepared as a mobile phase. The flow rate was set to 0.3 mL/minute, and the absorbance at the wavelength of 450 nm was measured.

(5) Results

Results are shown in Table 10 and FIG. 1. The β-cryptoxanthin concentration in blood at 60 minutes, at 120 minutes, and at 240 minutes after administration was significantly increased in the β-cryptoxanthin+yogurt group in comparison with the β-cryptoxanthin group. The area under the blood concentration curve (AUC) was significantly increased in the β-cryptoxanthin+yogurt group in comparison with the β-cryptoxanthin group. These results indicate that ingestion of the yogurt can promote absorption of β-cryptoxanthin. It is noted that the symbol "•" in the figure indicates that there is a significant difference relative to the β-cryptoxanthin group based on P<0.05.

TABLE 10

|  | β-Cryptoxanthin (pmol · min/mL) |
| --- | --- |
| β-Cryptoxanthin group | 16060 ± 313 |
| β-Cryptoxanthin + yogurt group | 25344 ± 1092* |

Average value ± standard deviation
* $P < 0.05$: there is a significant difference relative to the β-cryptoxanthin group.

Experiment 10: Promoting Absorption of Capsanthin (1) Yogurt Used

The yogurt used in Experiment 9 was used.

(2) Experimental Method 16 rats (SD, male, 8 weeks old, Japan SLC, Inc.) were acclimated for 7 days, and then, they were divided into the groups each having 8 rats. They were fasted for 18 hours, and then, capsanthin and a mixture of capsanthin and the yogurt each were administered to the rats of each group. Here, 5 mg/kg-body weight of capsanthin and 11.3 g/kg-body weight of the yogurt were administered. Blood sample was taken from a tail vein before the administration, as well as at 60 minutes, at 120 minutes, at 240 minutes, and at 480 minutes after the administration to obtain respective serums. For an easy-to-understand explanation, hereinafter, the rat group to which capsanthin was administered (control) is called "capsanthin group", and the rat group to which the mixture of capsanthin and the yogurt was administered (Example) is called "capsanthin+yogurt group".

(3) Measurement of Capsanthin 90 μL of a physiological salt solution and 300 μL of a dichloromethane-methanol solution (dichloromethane:methanol=1:2) were added to 50 μL of the serum. Next, 150 μL of hexane was further added to the resulting solution to extract capsanthin. The upper layer of the solution was transferred to a different tube, and then, the solvent was removed by nitrogen reflux. Then, the resulting product was dissolved into 150 μL of an ethyl acetate-methanol solution (ethyl acetate:methanol=30:70) containing 0.1% ammonium acetate to obtain an sample for HPLC.

(4) Condition of HPLC Analysis

For the HPLC measurement, the 1200 series (manufacture by Agilent Technologies, Inc.) was used. TSKgel ODS-80 TsQA (5.0×250 mm) (manufactured by Tosoh Corp.) was used as a column. Column temperature was set at 40° C. An ethyl acetate-methanol solution (ethyl acetate:methanol=30:70) containing 0.1% ammonium acetate was prepared as a mobile phase. The flow rate was set to 0.3 mL/minute, and the absorbance at the wavelength of 470 nm was measured.

(5) Results

Figure 2:
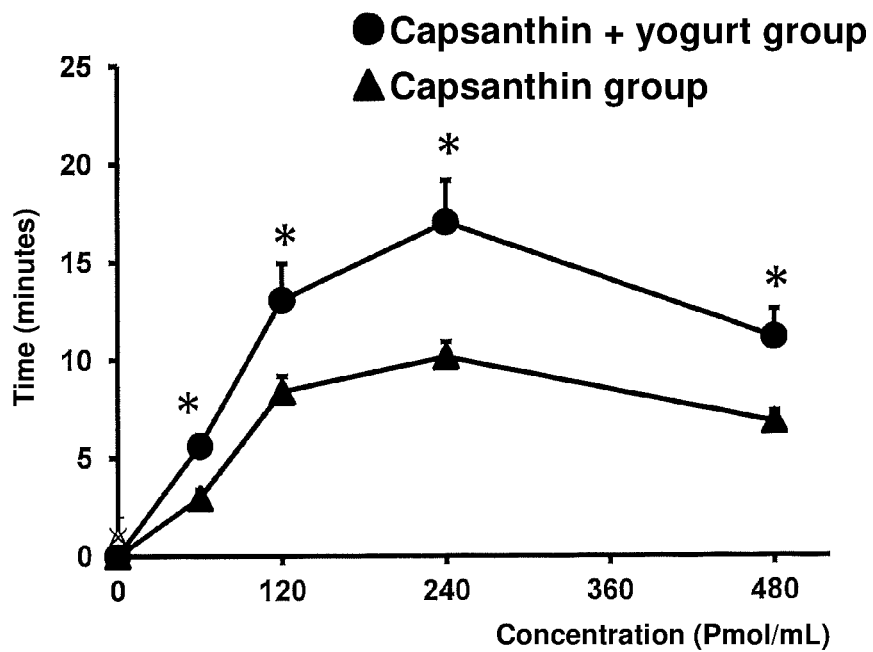
FIG. 2 A graph illustrating a change of a capsanthin concentration in a serum when capsanthin alone is administered, or capsanthin and a yogurt are administered simultaneously, to a rat.

Results are shown in Table 11 and FIG. 2. The capsanthin concentration in blood at 60 minutes, at 120 minutes, at 240 minutes, and at 480 minutes after administration was significantly increased in the capsanthin+yogurt group in comparison with the capsanthin group. The area under the blood concentration curve (AUC) was significantly increased in the capsanthin+yogurt group in comparison with the capsanthin group. These results indicate that ingestion of the yogurt can promote absorption of capsanthin. It is noted that the symbol "•" in the figure indicates that there is a significant difference relative to the capsanthin group based on P<0.05.

TABLE 11

| | Capsanthin (pmol · min/mL) |
|---|---|
| Capsanthin group | 3578 ± 232 |
| Capsanthin + yogurt group | 5914 ± 715* |

Average value ± standard deviation
* P < 0.05: there is a significant difference relative to the capsanthin group.

Experiment 11: Promoting Absorption of Hesperidin (1) Yogurt Used

The yogurt used in Experiment 9 was used.

(2) Experimental Method 16 rats (SD, male, 8 weeks old. Japan SLC, Inc.) were acclimated for 7 days, and then, they were divided into the groups each having 8 rats. They were fasted for 16 hours, and then, hesperidin and a mixture of hesperidin and the yogurt each were administered to the rats of each group. Here, 162 mg/kg-body weight of hesperidin and 11.3 g/kg-body weight of the yogurt were administered. Blood sample was taken from a tail vein before the administration, as well as at 60 minutes, at 120 minutes, and at 240 minutes after the administration to obtain respective serums. For an easy-to-understand explanation, hereinafter, the rat group to which hesperidin was administered (control) is called "hesperidin group", and the rat group to which the mixture of hesperidin and the yogurt was administered (Example) is called "hesperidin+yogurt group".

(3) Measurement of Hesperidin Metabolite

A hesperetin conjugate, which is a hesperidin metabolite, was measured as follows. 45 uL of a glucronidase solution (10,000 U/mL; manufactured by Sigma-Aldrich Corp.) dissolved in a 0.1 M sodium acetate buffer solution (pH 5.0), and 5 μL of a 0.1 M ascorbic acid solution dissolved in a 0.1 M sodium acetate buffer solution (pH 5.0) were added to 50 μL of the serum; and then, the resulting mixture was warmed at 37° C. for 2 hours. Then, 300 μL of methanol was added to the mixture to terminate the enzymatic reaction, and the mixture was centrifuged (at 12,000 rpm for 10 minutes at 4° C.). The supernatant thus obtained was transferred to a different tube, and then, the solvent was removed by centrifugal concentration. The resulting product was dissolved into 300 μL of a 50% acetonitrile solution containing 0.1% formic acid to prepare a sample for HPLC.

(4) HPLC Analysis Condition

For the HPLC measurement. Nexera XR (manufacture by Shimadzu Corp.) was used. As a MS/MS detector, 4500 QTRAP (manufactured by Sciex Pte. Ltd.) was used. As a column, ACQUITY UPLC HSS T3, 1.8 μm (2.1×50 mm) (manufactured by Waters Corp.) was used. Column temperature was set at 40° C. As for the mobile phase, a 0.1% formic acid solution was prepared as an A solution, and an acetonitrile solution containing 0.1% formic acid was prepared as a B solution. The column was kept with 30% of the B solution for 1 minute, and then, the concentration gradient of B solution was gradually changed up to 45% during a period of 4.5 minutes to elute a target substance. Then, the column was washed with 99% B solution for 2 minutes, and was kept with 30% B solution for 3 minutes. The flow rate was set to 0.3 mL/minute. The MS/MS analysis was carried out with an ESI negative mode. The MS/MS analysis was carried out under the following condition: a curtain gas flow rate of 30 psi; a collision gas flow rate of 9 psi; an ion spray voltage of −4500 V: a turbo gas temperature of 600° C., and an ion source gas of 70 psi.

(5) Results

Figure 3:
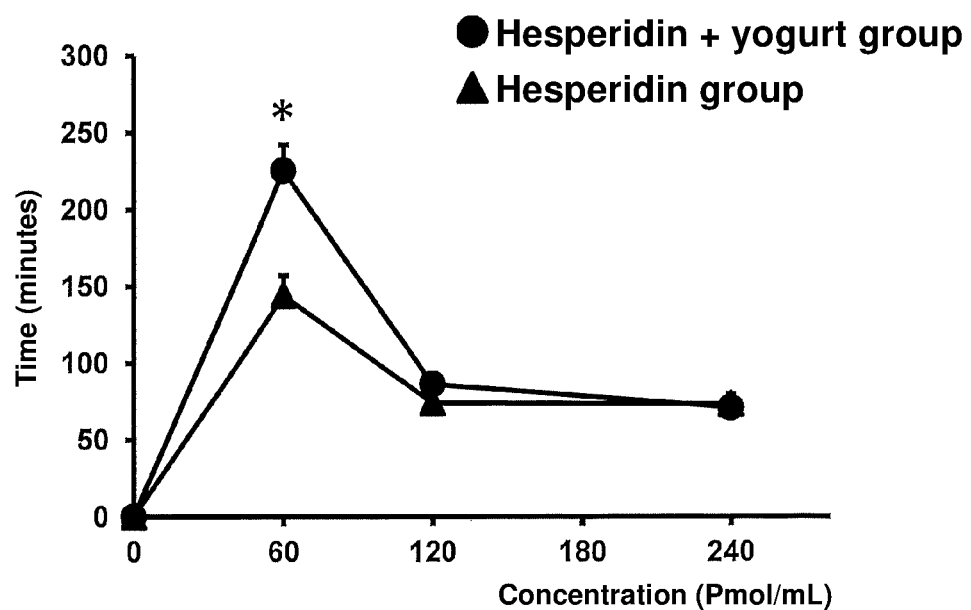
FIG. 3 A graph illustrating a change of a hesperetin conjugate concentration in a serum when hesperidin alone is administered, or hesperidin and a yogurt are administered simultaneously, to a rat.

Results are shown in Table 12 and FIG. 3. The hesperetin conjugate concentration in blood at 60 minutes after administration was significantly increased in the hesperidin+yogurt group in comparison with the hesperidin group. The area under the blood concentration curve (AUC) was significantly increased in the hesperidin+yogurt group in comparison with the hesperidin group. These results indicate that ingestion of the yogurt can promote absorption of the hesperetin conjugate. It is note that the symbol "•" in the figure indicates that there is a significant difference relative to the hesperidin group based on P<0.05.

TABLE 12

| | Hesperetin conjugate (pmol · min/mL) |
|---|---|
| Hesperidin group | 19699 ± 1368 |
| Hesperidin + yogurt group | 25559 ± 1729* |

Average value ± standard deviation
* P < 0.05: there is significant difference relative to the hesperidin group.

Experiment 12: Change of DH During Lactic Acid Bacterial Fermentation (1) Experimental Method Lactobacillus bulgaricus OLL1251 alone, and a combination of Lactobacillus bulgaricus OLL1251 and Streptococcus thermophilus OLS3290 each were applied to a culture medium containing 10% by mass of defatted powdered milk, and then, the culture medium was fermented at 43° C. to confirm the change of pH.

(2) Result

Result is shown in Table 13. The decrease in pH was faster in the fermentation with a combination of Lactobacillus bulgaricus OLL1251 and Streptococcus thermophilus OLS3290 in comparison with the fermentation with Lactobacillus bulgaricus OLL1251 alone. This indicates that action of the lactic acid bacterium is active and produces a larger amount of the polysaccharide. From the result, it was confirmed that the fermentation time to produce the polysaccharide can be shortened by combination of the bacteria.

TABLE 13

| | Lactobacillus bulgaricus OLL1251 | Lactobacillus bulgaricus OLL1251 and Streptococcus thermophilus OLS3290 |
|---|---|---|
| Before fermentation | 6.22 | 6.22 |
| 2 Hours | 5.86 | 5.68 |
| 3 Hours | 5.64 | 5.24 |
| 4 Hours | 5.47 | 4.86 |
| 5 Hours | 5.32 | 4.40 |
| 6 Hours | 5.23 | 4.18 |
| 7 Hours | 5.12 | 4.09 |
| 8 Hours | 5.11 | 3.99 |

Experiment 13: Promoting Absorption of
Carotenoid in Human (Addition to Carrot Juice)

(1) Preparation of Yogurt

*Lactobacillus bulgaricus* OLL1251 and *Streptococcus thermophilus* OLS3290 were applied to a culture medium containing 10% by mass of defatted powdered milk, and then, the culture medium was fermented at 40° C. until its pH reached 4.2. The yogurt thus obtained contained 90 μg/g of the polysaccharide.

(2) Experimental Method

The test was carried out to 16 male subjects with the age between 20 years old or more and 35 years old or less and with BMI between 18.5 kg/m$^2$ or more and 25.0 kg/m$^2$ or less. The subjects were fasted for 16 hours, and then, either a beverage containing 100 g of a carrot juice (a commercially available carrot juice containing 6 mg of α-carotene and 10 mg of β-carotene) and 100 g of water, or a beverage containing 100 g of said carrot juice and 100 g of the yogurt was ingested once into the subjects. After two weeks of wash-out, the beverage that was not ingested in the first ingestion test was ingested once into the subjects. The blood sample was taken before the ingestion of the test food, as well as at 2 hours, at 4 hours, at 6 hours, and at 8 hours after the ingestion to obtain the respective plasmas.

For an easy-to-understand explanation, hereinafter, the case that the carrot juice was ingested (control) is called "carrot juice group", and the case that the mixture of the carrot juice and the yogurt was ingested (Example) Is called "carrot juice+yogurt group".

(3) Results

Results are shown in Table 14. The areas under the plasma blood concentration-time curve (AUC) of α-carotene and of β-carotene were significantly increased in the carrot juice+yogurt group in comparison with the carrot juice group. This result indicates that in human the yogurt can promote absorption of the carotenoids contained in the carrot juice.

TABLE 14

|  | β-Carotene (pmol · hr/mL) | α-Carotene (pmol · hr/mL) |
|---|---|---|
| Carrot juice group | 92.5 ± 14.2 | 70.8 ± 10.2 |
| Carrot juice + yogurt group | 161.8 ± 18.8* | 115.7 ± 12.1* |

Average value ± standard deviation
* P < 0.05: there is a significant difference relative to the carrot juice group.

Experiment 14: Promoting Absorption of
Carotenoid in Human (Addition to Tomato Juice)

(1) Preparation of Yogurt

*Lactobacillus bulgaricus* OLL1251 and *Streptococcus thermophilus* OLS3290 were applied to a culture medium containing 10% by mass of defatted powdered milk, and then, the culture medium was fermented at 40° C. until its pH reached 4.2. The yogurt thus obtained contained 90 μg/g of the polysaccharide.

(2) Experimental Method

The test was carried out to 15 male subjects with the age between 20 years old or more and 35 years old or less and with BMI between 18.5 kg/m$^2$ or more and 25.0 kg/m$^2$ or less. The subjects were fasted for 16 hours, and then, either a beverage containing 100 g of a tomato juice (a commercially available tomato juice (containing 10 mg of lycopene)) and 100 g of water, or a beverage containing 100 g of said tomato juice and 100 g of the yogurt was ingested once into the subjects. After two weeks of wash-out, the beverage that was not ingested in the first ingestion test was ingested once into the subjects. The blood sample was taken before the ingestion of the test food, as well as at 2 hours, at 4 hours, at 6 hours, and at 8 hours after the ingestion to obtain respective plasmas.

For an easy-to-understand explanation, hereinafter, the case that the tomato juice was ingested (control) is called "tomato juice group", and the case that the mixture of the tomato juice and the yogurt was ingested (Example) Is called "tomato juice+yogurt group".

(3) Results

Results are shown in Table 15. The area under the plasma blood concentration-time curve (AUC) of lycopene was significantly increased in the tomato juice+yogurt group in comparison with the tomato juice group. This result indicates that in human the yogurt can promote absorption of the carotenoid contained in the tomato juice.

TABLE 15

|  | Lycopene (pmol · hr/mL) |
|---|---|
| Tomato juice group | 2.6 ± 3.6 |
| Tomato juice + yogurt group | 16.5 ± 2.9* |

Average value ± standard deviation
* P < 0.05: there is a significant difference relative to the tomato juice group.

Experiment 15: Promoting Absorption of
Carotenoid in Human (Addition to Spinach Juice)

(1) Preparation of Yogurt

*Lactobacillus bulgaricus* OLL1261 and *Streptococcus thermophilus* OLS3290 were applied to a culture medium containing 10% by mass of defatted powdered milk, and then, the culture medium was fermented at 40° C. until its pH reached 4.2. The yogurt thus obtained contained 90 μg/g of the polysaccharide.

(2) Experimental Method

The test was carried out to 16 male subjects with the age between 20 years old or more and 35 years old or less and with BMI between 18.5 kg/or more and 25.0 kg/m$^2$ or less. The subjects were fasted for 16 hours, and then, either a beverage containing 100 g of a spinach juice (a commercially available spinach juice containing 4.0 mg of lutein and 2.4 mg of β-carotene) and 100 g of water, or a beverage containing 100 g of said spinach juice and 100 g of the yogurt was ingested once into the subjects. After two weeks of wash-out, the beverage that was not ingested in the first ingestion test was ingested once into the subjects. The blood sample was taken before the ingestion of the test food, as well as at 2 hours, at 4 hours, at 6 hours, and at 8 hours after the ingestion to obtain respective plasmas.

For an easy-to-understand explanation, hereinafter, the case that the spinach juice was ingested (control) is called "spinach juice group", and the case that the mixture of the spinach juice and the yogurt was ingested (Example) is called "spinach juice+yogurt group".

(3) Results

Results are shown in Table 16. The areas under the plasma blood concentration-time curve (AUC) of lutein and of β-carotene were significantly increased in the spinach juice+yogurt group in comparison with the spinach juice group. This result indicates that in human the yogurt can promote absorption of the carotenoids contained in the spinach juice.

TABLE 16

|  | Rutin (pmol · hr/mL) | β-Carotene (pmol · hr/mL) |
|---|---|---|
| Spinach juice group | −52.1 ± 14.0 | −2.2 ± 3.3 |
| Spinach juice + yogurt group | 31.6 ± 7.4* | 10.5 ± 5.9* |

Average value ± standard deviation
* P < 0.05: there is a significant difference relative to the spinach juice group.

Experiment 16: Promoting Absorption of Carotenoid in Human (Addition to Mandarin Orange Juice)

(1) Preparation of Yogurt

*Lactobacillus bulgaricus* OLL1251 and *Streptococcus thermophilus* OLS3290 were applied to a culture medium containing 10% by mass of defatted powdered milk, and then, the culture medium was fermented at 40° C. until its pH reached 4.2. The yogurt thus obtained contained 90 μg/g the polysaccharide.

5 male subjects were fasted for 12 hours, and then, 100 g of a commercially available mandarin orange juice (containing 3 mg of β-cryptoxanthin) was ingested into the subjects. At 4 hours after the ingestion, their serum were taken. After one week of wash-out, a mixture of 100 g of said mandarin orange juice and 100 g of the yogurt was ingested into the subjects, and 4 hours after the ingestion, their serums were taken.

(3) Results

Results are shown in Table 17. Amount of change in β-cryptoxanthin concentration in the plasma before and after the ingestion of the mandarin orange juice was significantly increased in the mandarin orange juice+yogurt group in comparison with the mandarin orange juice group. This result indicates that in human, fermentation with the lactic acid bacterium promotes absorption of the carotenoid contained in the mandarin orange juice.

TABLE 17

|  | β-Cryptoxanthin (Δpmol/mL) |
|---|---|
| Mandarin Orange juice group | 5.3 ± 7.5 |
| Mandarin Orange juice + yogurt group | 20.1 ± 9.6* |

Average value ± standard deviation
* P < 0.05: there is a significant difference relative to the mandarin orange juice group.

What is claimed is:

1. A method for promoting the intake of a poorly water-soluble phytochemical into blood of a human or an animal, comprising the step of administering or ingesting a polysaccharide-containing lactic acid bacterial product together with a poorly water-soluble phytochemical orally to the human or the animal in need thereof,
   wherein the lactic acid bacterial product is a product produced by *Lactobacillus delbrueckii* ssp. *bulgaricus* OLL1251 with an accession number NITE BP-02703.

2. The method according to claim 1, wherein the lactic acid bacterial product is a product produced by a combination of *Lactobacillus delbrueckii* ssp. *bulgaricus* OLL1251 with an accession number NITE BP-02703 and *Streptococcus thermophilus* OLS3290 with an accession number FERM BP-19638.

3. The method according to claim 1, wherein the poorly water-soluble phytochemical has the dissolution rate in water of 88% or less.

4. The method according to claim 1, wherein the poorly water-soluble phytochemical has the dissolution rate in water of 50% or less.

5. The method according to claim 1, wherein the poorly water-soluble phytochemical is selected from the group consisting of a polyphenol, an organic sulfur compound, and a terpenoid.

6. The method according to claim 5, wherein the polyphenol is a flavonoid.

7. The method according to claim 6, wherein the flavonoid is selected from the group consisting of flavone, isoflavone, flavonol, flavanone, flavan-3-ol, anthocyanin, and an analogue thereof.

8. The method according to claim 7, wherein the flavonoid is flavone, isoflavone, flavonol, flavanone, flavan-3-ol, or an analogue thereof.

9. The method according to claim 5, wherein the terpenoid is tetraterpene and an analogue thereof.

10. The method according to claim 1, wherein the poorly water-soluble phytochemical is selected from quercetin, genistein, epicatechin, luteolin, naringenin, hesperidin, β-carotene, α-carotene, β-cryptoxanthin, capsanthin, lutein, lycopene, and an analogue thereof.

11. The method according to claim 1, wherein the lactic acid bacterial product is fermented milk.

12. The method according to claim 1, wherein the polysaccharide-containing lactic acid bacterial product is administered or ingested in a form of a composition comprising, as an active ingredient, the polysaccharide-containing lactic acid bacterial product.

13. The method according to claim 12, wherein the polysaccharide-containing lactic acid bacterial product is administered or ingested in a form of a food additive comprising the composition comprising, as an active ingredient, the polysaccharide-containing lactic acid bacterial product.

14. The method according to claim 12, wherein the polysaccharide-containing lactic acid bacterial product is administered or ingested in a form of a food, or a beverage, or a food or beverage composition, comprising the composition comprising, as an active ingredient, the polysaccharide-containing lactic acid bacterial product.

15. The method according to claim 1, further comprising the step of producing a polysaccharide-containing lactic acid bacterial product by fermenting *Lactobacillus delbrueckii* ssp. *bulgaricus* OLL1251 with an accession number NITE BP-02703, wherein the polysaccharide-containing lactic acid bacterial product of the administering or ingesting step is the product obtained from the producing step.

16. The method according to claim 15, wherein *Lactobacillus delbrueckii* ssp. *bulgaricus* OLL1251 with an accession number NITE BP-02703 is fermented in animal milk or a processed product thereof.

17. The method according to claim 1, further comprising the step of fermenting animal milk with *Lactobacillus delbrueckii* ssp. *bulgaricus* OLL1251 with an accession number NITE BP-02703 to produce polysaccharide, and the polysaccharide-containing lactic acid bacterial product of the administered or ingested step is the product containing the polysaccharide produced from the fermenting step.

* * * * *